United States Patent [19]

Abramowitz

[11] Patent Number: 5,360,341
[45] Date of Patent: Nov. 1, 1994

[54] METHOD AND APPLIANCE FOR PROMOTING THE HEALING OF ORAL TISSUES

[76] Inventor: Paul N. Abramowitz, 1418 Westwood La., Wynnewood, Pa. 19096

[21] Appl. No.: 99,413

[22] Filed: Jul. 30, 1993

[51] Int. Cl.$^5$ ............................ A61C 5/00; A61C 5/14
[52] U.S. Cl. .................................... 433/215; 433/136; 606/213; 128/DIG. 14
[58] Field of Search ............... 433/136, 138, 172, 173, 433/174, 175, 176, 215, 229; 602/58; 606/213, 214, 215, 216; 128/846, 849, 850, 851, 852, 853, 854, 855, 856, DIG. 14

[56] References Cited

U.S. PATENT DOCUMENTS

| | | | |
|---|---|---|---|
| 300,600 | 6/1884 | Halsey | 433/136 |
| 671,929 | 4/1901 | Horgan | 433/136 |
| 2,012,755 | 8/1935 | De Muth | 602/58 X |
| 2,421,193 | 5/1947 | Gardner | 606/215 |
| 2,943,623 | 7/1960 | Thompson | 128/DIG. 14 |
| 3,113,568 | 12/1963 | Robins | 606/215 X |
| 4,872,840 | 10/1989 | Bori | 433/173 |
| 5,032,445 | 7/1991 | Scantlebury et al. | 433/215 X |
| 5,197,882 | 3/1993 | Jernberg | 433/215 |

OTHER PUBLICATIONS

"Gore-Tex Augmentation Material", by W. L. Gore & Associates, Sep. 1991.
"Gore Regenerative Technologies Order Information", by W. L. Gore & Associates, Sep. 1992.
"Important Considerations Regarding Trimming and Placing Gore-Tex Periodontal Material, etc.", W. L. Gore & Associates, Sep. 1992.

*Primary Examiner*—Gene Mancene
*Assistant Examiner*—Nicholas D. Lucchesi
*Attorney, Agent, or Firm*—William H. Eilberg

[57] ABSTRACT

A dental appliance promotes the healing of oral tissues, such as bone tissue, cementum, and periodontal ligament destroyed by periodontal disease. The appliance includes a flat piece of elastic material, connected at its two opposing edges to two pieces of a biocompatible membrane. The elastic material has one or more punch holes which allow the material to be fitted around a patient's teeth. The elastic material forms a barrier which protects the area of damaged tissue, and promotes regeneration of that tissue. The elastic seal minimizes intrusion of saliva and bacteria into the diseased area, and it is easily cleaned, thus preventing harmful bacteria from colonizing on the material, and prolonging the time during which the appliance can remain in the mouth. The membrane is held under the patient's gums. Due to the biocompatibility of the membrane, gum tissue becomes attached to the membrane, so that the appliance is firmly held in place for an extended period of time. Thus, the appliance can be held in place for a sufficient period to enable the damaged tissue to regenerate. The invention also includes the method of inserting and using the appliance.

20 Claims, 2 Drawing Sheets

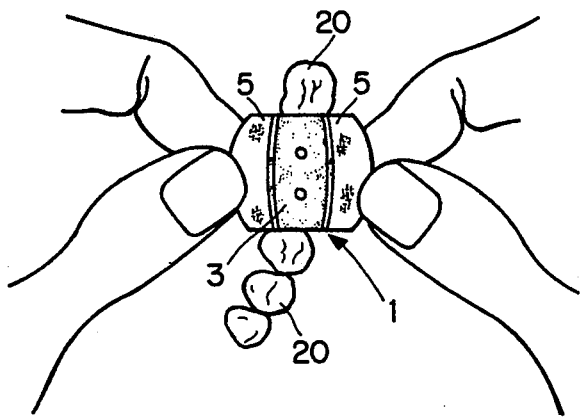
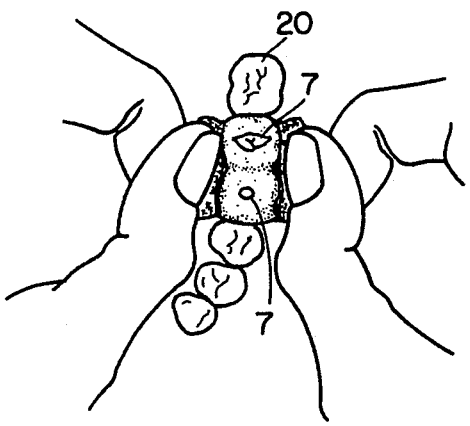
Fig. 4a    Fig. 4b
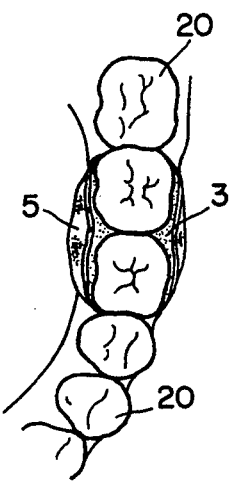
Fig. 4c
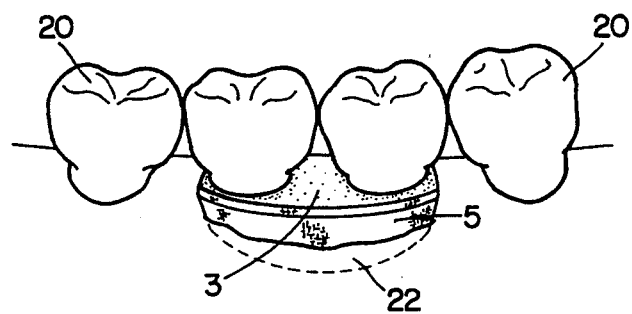
Fig. 5

METHOD AND APPLIANCE FOR PROMOTING THE HEALING OF ORAL TISSUES

BACKGROUND OF THE INVENTION

This invention relates to the field of oral surgery, and, more specifically, periodontal surgery. The invention provides a method and appliance for promoting the healing of oral tissues which have been damaged by disease.

Periodontal disease occurs when bacteria (plaque) multiply on the teeth and gums. If the bacteria are not removed, they eventually cause inflammation of the gums, and destroy the gum tissue. The condition becomes still worse when the bacterial infection approaches the underlying bone. In many cases, some of the bone will have been eaten away as a consequence of periodontal disease, before the patient seeks treatment.

The bone tissue which is lost to periodontal disease can be regenerated automatically by the body, with the passage of time. One can promote rapid regeneration of the bone tissue by isolating the bone from other tissues in its vicinity, and especially from the gum tissue overlying the bone. To provide such isolation, it has been known to use a physical barrier to separate the bone tissue from surrounding tissues. A barrier can also be used to promote regeneration of other oral tissues, such as the cementum, which is on the tooth, and the periodontal ligament, which joins the tooth (via the cementum) to the bone. Such a barrier allows the bone tissue, or other oral tissues, to regenerate itself without "competition" from other surrounding tissues, specifically gum tissue. In the absence of a barrier, surrounding tissues (such as gum tissue) would fill the empty space formerly occupied by the bone and periodontal ligament, and would tend to prevent the bone from fully restoring itself to its former condition. The barrier therefore provides means for favoring the regeneration of the damaged bone, cementum, and periodontal ligament over the growth of other oral tissues, specifically gum tissue.

One material which has been found useful in forming the above-described barrier is polytetrafluoroethylene (PTFE), also known by the trademark TEFLON. In particular, it has been known to use a periodontal barrier made of a specific form of TEFLON, sold by W. L. Gore & Associates, Inc. under the trademark GORE-TEX. GORE-TEX periodontal materials are commercially available, and are provided in the form of generally flat membranes having various sizes and shapes. These membranes have been widely used to promote regeneration of damaged oral tissues.

The major advantage of the GORE-TEX material, when used as the periodontal barrier described above, is that the material is biocompatible. That is, oral tissues (particularly gum tissue) will become attached to the GORE-TEX membrane, holding the membrane in place while the process of tissue regeneration proceeds. Regeneration of the supporting structures of a tooth, i.e. bone, cementum, and periodontal ligament, requires that the barrier membrane be kept in place for at least 4–6 weeks. However, the longer the barrier is allowed to remain in position, the more likely one is to obtain a more mature and stable regenerative result.

The GORE-TEX membrane has not been entirely successful as a periodontal barrier. Regardless of how tightly one tries to fasten the GORE-TEX membrane around the tooth, there always exists a space between the tooth and the membrane, and this space allows saliva and bacteria to percolate into the healing area. Exposure of the membrane promotes the growth of harmful bacteria, often necessitating the removal of the membrane before the healing process is complete. More importantly, when the membrane is prematurely removed, the newly-regenerated tissue is exposed. Because of its fragile nature, the new regenerated tissue can often be wiped away with a dental instrument, nullifying some of the effect of weeks of healing.

The present invention provides a periodontal barrier which promotes the healing of oral tissues, such as bone, cementum, and periodontal ligament, and which also overcomes the disadvantages discussed above.

SUMMARY OF THE INVENTION

The present invention includes an appliance which is fitted over one or more of a patient's teeth. The appliance includes a piece of smooth elastic material which can function as a barrier to protect a wound while healing takes place. The elastic material has two opposing edges, each edge being attached to a selectively permeable biocompatible membrane. The elastic material is preferably rubber or its equivalent, and the membrane is preferably made of polytetrafluoroethylene. The elastic material is occlusive, i.e. it does not allow oral tissue to grow through it.

Before the appliance can be used, one or more small holes are punched in the elastic material. These holes enable the material to be drawn tightly over one or more of the patient's teeth, with the teeth protruding through the punch holes in a "poncho" style. When the elastic material is so inserted, the material forms a tight seal around the tooth, and also comprises a barrier which protects the area in which tissue is to be regenerated.

At the same time, the biocompatible membrane is inserted under the flaps of the patient's gum, i.e. buccal and lingual or palatal surfaces. The membrane allows other oral tissues to grow onto and through the membrane, and to become attached to the membrane and anchor it in place. Due to the attachment of oral tissues to the membrane, the entire appliance can remain in the patient's mouth for an extended period of time. Because of the occlusive property of the elastic material, and due to its smooth surface, the appliance is unlikely to harbor harmful bacteria, and the appliance can be kept in the mouth for a sufficient time to promote proper healing of the bone tissues.

The invention also includes the method of using the appliance described above, for the purpose of promoting healing of oral tissues. In the method of the invention, one provides an appliance as described above. One punches the elastic material to form the proper sized holes. A larger diameter hole would be used for a posterior tooth and a narrower hole for an anterior tooth. The latter arrangement insures maximal sealing effect when the elastic material is placed around the tooth. One then forces the elastic material over one or more of the patient's teeth, until the teeth protrude through the punch holes. One firmly holds the biocompatible membrane under the patient's gum. The gum tissue is then closed back over the barrier. The appliance is then allowed to remain in the patient's mouth for a time sufficient to allow the bone tissue, cementum, and periodontal ligament to regenerate.

The present invention therefore has the primary object of providing an appliance and method for promoting the healing of oral tissues, especially bone tissues, cementum, and periodontal ligament.

The invention has the further object of improving the effectiveness of periodontal treatment, by enhancing the prospect for successful regeneration of oral tissues, as compared with techniques of the prior art.

The invention has the further object of providing a method and device for promoting the healing of bone tissue that has been damaged by periodontal disease.

The invention has the further object of providing a method and appliance as described above, wherein the appliance can be retained in the mouth, due to natural attachment to oral tissues, and due to a tight seal around the neck of an involved tooth, for a time sufficient to allow proper healing of oral tissues.

The invention has the further object of providing a method and appliance wherein bone alone can be regenerated around oral implants.

The reader skilled in the art will recognize other objects and advantages of the present invention, from a reading of the following brief description of the drawings, the detailed description of the invention, and the appended claims.

BRIEF DESCRIPTION OF THE DRAWINGS

FIGS. 4a-4c illustrate the process of inserting the appliance over a pair of teeth, with FIG. 4c showing the appliance inserted to the point where the teeth protrude through the appliance.

FIG. 5 shows a side view of the appliance of the present invention, after it has been inserted over a pair of teeth.

DETAILED DESCRIPTION OF THE INVENTION

Figure 1:
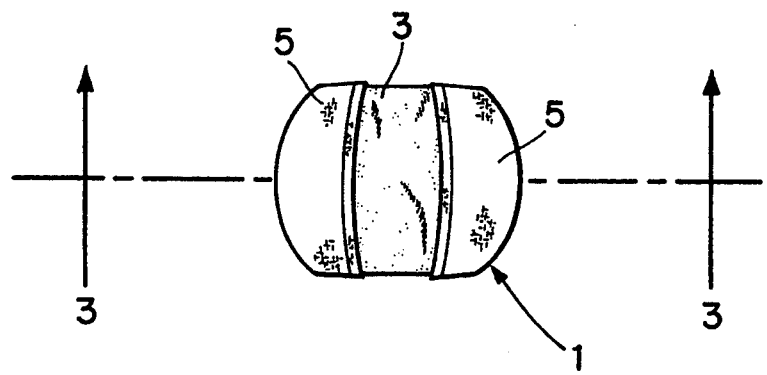
FIG. 1 provides a top view of the appliance made according to the present invention.
Figure 2:
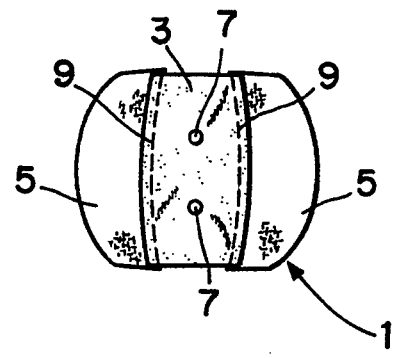
FIG. 2 provides a bottom view of the appliance, and also shows an alternative means of joining the components of the appliance. It also shows punch holes formed in the elastic material.
Figure 3:
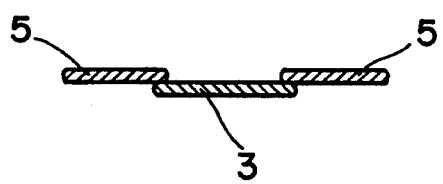
FIG. 3 shows a cross-sectional view of the appliance, taken along the line 3—3 of FIG. 1.

FIGS. 1-3 show the structure of the appliance made according to the present invention. As shown in FIG. 1, appliance i includes rubber dam 3 and biocompatible membrane pieces 5. Of FIGS. 1-3, only FIG. 2 shows punch holes 7, which are intended to allow the rubber dam to fit snugly around the teeth. It is preferred that the appliance be provided initially without the punch holes, so that the practitioner can punch out the holes after analyzing the particular situation of the patient. However, the appliance could also be provided with pre-punched holes, and the invention is not limited to either case. FIGS. 1-3 are therefore intended to illustrate both alternatives.

In the embodiment of FIG. 2, there are two punch holes, and the appliance shown can therefore fit over two adjacent teeth. One can vary the length of the rubber dam, and the number of punch holes, within the scope of the invention. Thus, the rubber dam can be made long enough to fit over more than two teeth, and the biocompatible membrane can be correspondingly lengthened. One can also vary the width of the rubber dam. The punch holes are preferably formed, by the practitioner, at or near the center of the rubber dam, depending on how many teeth are diseased. One can make the holes in the rubber dam with a standard punch which is commercially available and commonly used by dentists.

The membrane pieces 5 can be attached to the rubber dam 3 by using an adhesive, such as a cyanoacrylate glue, or other glue, or by sewing the components together. FIG. 2, which shows a bottom view of the appliance, also represents the case in which the components are sewn. Thus, FIG. 2 shows stitch lines 9. It is understood that either means of attachment can be used, and the embodiments of FIGS. 1 and 2 are otherwise equivalent.

The shape of the rubber dam 3 is not critical, but it should be long enough to span the teeth in the area of the diseased tissue, and should be wide enough to provide an effective seal for the area in the vicinity of the tooth. However, the rubber dam should not extend across the full width of the appliance, because one wants to allow gum tissue, from above, and existing bone, from below, to have access to the membrane. Neither the gum tissue nor the bone can become attached to the membrane if the tissue is blocked by the rubber dam. This would result in early exposure of the entire barrier early in treatment, a situation seen when using the rubber dam alone.

The shapes of the membrane pieces 5 are also not critical, but the pieces should be large enough to enable the appliance to be conveniently grasped during insertion, and also large enough to provide ample surface area so that gum tissue and underlying bone will readily become attached to them.

FIG. 3 shows a cross-sectional view of the appliance of FIG. 1. FIG. 3 shows membrane pieces 5 located above the rubber dam 3, but it is also possible to position them below the rubber dam, within the scope of the invention. FIG. 3 explicitly shows that the rubber dam does not extend across the full width of the appliance; as shown in FIG. 3, the area of overlap between the membrane and the rubber dam is relatively small.

FIGS. 4a, 4b, and 4c show the steps of the process of insertion of the appliance of the present invention. FIG. 4a shows the appliance 1 being grasped along the membrane pieces 5 and held over a row of the patient's teeth 20. Note that, during insertion, the membrane pieces serve as handles which can be gripped by the dentist's fingers. In the embodiment shown in FIGS. 4a-4c, there are two punch holes in the rubber dam 3, so the appliance fits over two teeth. In FIG. 4b, the appliance is being pressed onto the teeth, with the holes being stretched so that the teeth will protrude through those holes. The dentist's fingers are still gripping the membrane pieces, as shown in FIG. 4b, urging the appliance towards the roots of the teeth and down onto the bone. The appliance is forced either up or down, depending on whether it is being inserted around the upper or the lower teeth. FIG. 4c shows a top view of the appliance after it has been inserted, with the membrane pieces resting against the underlying bone, and the teeth protruding through the appliance. For clarity of illustration, FIG. 4 does not show the flaps of gum over the membrane. FIG. 5 provides a side view of one of the membrane pieces of the appliance, after the appliance has been inserted over the teeth. FIG. 5 shows gum 22 extending over one of the membrane pieces. For clarity of illustration, the gum in FIG. 5 is broken-away so that the membrane piece 5 is plainly visible.

The rubber dam may be rubber, or it may be formed of any other occlusive, smooth, elastic material that can be provided in the form of a thin sheet. What is important is that the rubber dam fit tightly around the tooth, that it form a barrier to growth of gum tissues into the diseased area, and that it prevent saliva and bacteria from entering the area of the regenerating tissue. The rubber dam can be made of the same type of material that has been known in dentistry for temporarily isolating one tooth from the others, and from the tongue, during a root canal procedure. However, the use of the material as a periodontal barrier is new. Moreover, it has been found that, when the rubber dam is used alone, i.e. without the selectively permeable membrane, the results are unsatisfactory, due to the tendency of the gum to retract from the rubber, causing early exposure of tissue and thus early removal from the mouth.

The smoothness of the rubber dam is also important, because a smooth material can be easily cleansed. Also, making the material smooth further tends to prevent the accumulation of pathogenic bacteria, reducing the risk of having to remove it due to infection, before treatment is completed.

The biocompatible membrane is preferably made of a polytetrafluoroethylene (TEFLON) material, and most preferably is made of the material sold by W. L. Gore & Associates, Inc., under the trademark "GORE-TEX". The membrane is selectively permeable to oral tissues, and allows selective growth of oral tissues through it, thus anchoring the membrane in place. Selective permeability, as used herein, means that the membrane will allow some, but not all, tissue to pass through it. It is generally the size of the cells of the tissue that determines whether that tissue can pass through the membrane.

The biocompatible membrane and/or the rubber dam could also be made of a biodegradable material, i.e. a material that disintegrates in the body with the passage of time. Of course, such material must not disintegrate until a sufficient time has passed to allow proper healing. The advantage of a biodegradable material is that it avoids the need for an additional surgical procedure to remove the appliance after treatment is complete. The present invention is therefore intended to include the cases in which either, neither, or both of the membrane and the rubber dam are made of biodegradable material.

It is also possible that a material could be found which is both biocompatible and elastic. Such a material could also be biodegradable. The invention is also intended to include the case in which both the membrane and the rubber dam are made of the same material. Such material may or may not also be biodegradable.

The present invention also includes the method of using the appliance described above. The method is used after the practitioner has performed conventional periodontal surgery, which surgery normally includes cutting a portion of the gums away from both sides of the teeth and making incisions in the gums, between the teeth. According to the method of the present invention, one provides the appliance described, and punches holes in it, to accommodate the teeth over which the appliance is to be inserted. One inserts the appliance over the teeth, to the point wherein the tooth protrudes through the elastic material portion, and the elastic material portion abuts the bone in the diseased area. The pieces of biocompatible material are inserted between the gum and the bone, so that a flap of gum tissue holds the biocompatible material against the bone. The flaps of gum are then sutured together to close the wound created by the surgical procedure. The appliance is then held in place for a sufficient time to allow healing of the diseased tissues.

The appliance of the present invention protects the regenerating tissue in two main ways. First, the rubber dam acts as a barrier which isolates the bone tissue, the periodontal ligament, and the cementum from the gum tissue, thereby promoting regeneration of the periodontal ligament, cementum, and bone. As explained above, oral bone tissue can regenerate with time, and the regeneration process is enhanced when the barrier prevents the fill-in of other oral tissues into the area of bone growth. Secondly, the attachment of gum tissue to the biocompatible membrane means that the gum cannot retract from its collar-like abutment around the tooth. Thus, to a certain extent, the gum provides additional protection for the wound, prolonging its proximity to the healing area and preventing retraction and early exposure of the membrane.

While the primary function of the membrane is to anchor the appliance to the gums, and to the underlying existing bone, the membrane may also act as a barrier to some extent, further isolating the area of regenerating bone tissue, cementum, and periodontal ligament, from other oral tissues.

In summary, the appliance of the present invention provides a tight seal around the tooth, thus reducing the amount of percolation of saliva and bacteria into the healing area. Moreover, because the rubber dam material is smooth, it is easily cleaned if exposure to bacteria does occur. Thus, the likelihood of infection is reduced, resulting in prolonged use and greater regenerative potential. The biocompatible membrane serves to anchor the appliance in the patient's mouth while also providing some additional isolation of the damaged tissue. Thus, due to the action of the membrane, the gum does not tend to retract from the tooth during the healing process. And because the membrane is firmly anchored due to tissue growth, the appliance can remain in the patient's mouth for an extended period of time, long enough to promote proper healing of bone tissue, cementum, and periodontal ligament.

The invention can also be used for promoting the regeneration of bone in the vicinity of oral implants. It is well-known in dentistry to provide osseointegrated implants, which may take the form of titanium rods inserted into the bone, in the area where a patient has lost teeth. The rods become supports for artificial teeth. The above-described implants are commercially available, for example, from the Branemark company of Sweden or IMZ of Germany. One seeks to promote bone growth in the area of the implants, but many times the patient loses bone in those areas. It has been known to use a membrane, such as GORE-TEX to promote bone growth around these rods. It is believed that the present invention will work much better in promoting bone growth in the area of such implants.

Figure 6:
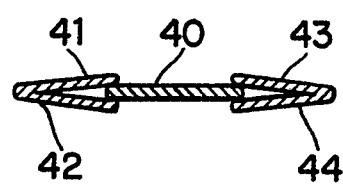
FIG. 6 provides a cross-sectional view, from the same perspective as FIG. 3, and shows an alternative embodiment in which the rubber material is sandwiched between pieces of the biocompatible membrane.

FIG. 6 shows an alternative construction of the appliance of the present invention. FIG. 6 is a cross-sectional view taken from the same perspective as that of FIG. 3. In the embodiment of FIG. 6, the ends of rubber dam 40 are sandwiched between pairs of membrane pieces. In particular, one end of the rubber dam is sandwiched between membrane pieces 41 and 42, which pieces are sutured or otherwise joined together. The other end of the rubber dam is sandwiched between membrane pieces 43 and 44, in a similar manner. Thus, in the embodiment of FIG. 6, the membrane pieces are effectively formed in two layers, with the rubber dam being sandwiched between the two layers. The latter embodiment provides membrane pieces which are more sturdy, and provides a more secure attachment of the rubber dam to the membrane pieces.

Note that the present invention offers substantial and surprising advantages over appliances consisting of a rubber dam or a biocompatible membrane taken alone. If the rubber dam is used alone, it tends to lift itself from under the gum tissue and becomes fully exposed, thus limiting the time during which the appliance can be kept in place. If the biocompatible membrane is used alone, it tends to attract bacteria when exposed, and becomes infected to the point that removal is necessary. With the present invention, even if the rubber dam portion does become exposed, it does not need to be removed so early in the treatment, because its smooth surface allows easy cleaning by the patient, and bacterial colonization can be prevented or minimized.

One can modify the present invention in other ways. The specific shapes and sizes of the membrane pieces and the rubber dam can be varied. Different materials can be substituted, provided that the equivalent of the rubber dam comprises a good barrier for protecting the area of regenerating tissue, and provided that the membrane be capable of natural attachment to the gum tissues. Different means for attaching the rubber dam to the membrane can be used. These and other modifications, which will be apparent to those skilled in the art, should be considered within the spirit and scope of the following claims.

What is claimed is:

1. A method of promoting healing of oral tissues of a patient, the method comprising the steps of:
   a) providing an appliance comprising an elastic material, the elastic material having at least two edges, the appliance also including a pair of pieces of selectively permeable biocompatible material, said pieces being attached to the at least two edges of the elastic material,
   b) punching at least one hole in the elastic material,
   c) inserting said appliance over at least one tooth of the patient, the tooth being implanted within bone, the tooth being adjacent to gum tissue, the insertion step being performed by forcing the elastic material over the at least one tooth until the at least one tooth protrudes through said at least one hole, and until the elastic material abuts the bone,
   d) holding said pieces of biocompatible material against the bone while affixing the gum tissue over the biocompatible material, and
   e) allowing the appliance to remain in place for a sufficient time to promote healing of said tissues.

2. The method of claim 1, wherein the holding step includes the step of pressing the pieces firmly against the bone.

3. The method of claim 1, wherein the inserting step is preceded by the step of setting the appliance against the bone near the at least one tooth.

4. The method of claim 1, wherein the elastic material is totally occlusive.

5. A method of promoting the healing of damaged oral tissues of a patient, the method comprising the steps of:
   a) inserting an appliance over one or more teeth of the patient, in an area near the damaged tissues, the one or more teeth being implanted within bone, the appliance including a perforated occlusive elastic material and at least one biocompatible material attached to the elastic material, the inserting step being performed such that the elastic material fits around at least one tooth and the biocompatible material is set in place between the bone and overlying gum tissue, and
   b) allowing the appliance to remain in place until the damaged tissues have healed.

6. The method of claim 5, wherein the inserting step includes the step of setting the at least one biocompatible material firmly under the gum, so that the gum can become attached to the biocompatible material when the gum is replaced around the at least one tooth.

7. An appliance for promoting healing of diseased oral tissues, the appliance comprising:
   a) a generally flat piece of elastic material, the elastic material having at least two edges, and
   b) a pair of pieces of biocompatible material, the biocompatible material being made of polytetrafluoroethylene, said pieces of biocompatible material being attached to the at least two edges of the elastic material.

8. The appliance of claim 7, wherein the elastic material is totally occlusive with respect to the oral tissues.

9. The appliance of claim 7, wherein the elastic material is rubber.

10. The appliance of claim 7, wherein the biocompatible material is selectively permeable.

11. The appliance of claim 7, wherein the biocompatible material is glued to the elastic material.

12. The appliance of claim 7, wherein the biocompatible material is sutured to the elastic material.

13. The appliance of claim 7, wherein the elastic material has at least one hole, the at least one hole being capable of admitting a tooth of a patient.

14. The appliance of claim 13, wherein the elastic material has a plurality of holes, the holes being arranged to receive a plurality of teeth of a patient.

15. The appliance of claim 7, wherein at least one of the pieces of biocompatible material is formed in two layers, and wherein the elastic material is sandwiched between said layers.

16. An appliance for promoting healing of diseased oral tissues, the appliance comprising:
   a) a generally flat piece of elastic material, the elastic material being totally occlusive with respect to biological tissues, the elastic material having two opposing edges, and
   b) a pair of pieces of a generally flat biocompatible material, the biocompatible material being made of polytetrafluoroethylene, said pieces of biocompatible material being attached to the opposing edges of the elastic material.

17. The appliance of claim 16, wherein the elastic material is rubber.

18. The appliance of claim 16, wherein each piece of the biocompatible material is formed in at least two layers, the at least two layers being joined together, wherein the elastic material is sandwiched between the at least two layers.

19. The appliance of claim 16, wherein the elastic material has at least one hole, the at least one hole being capable of admitting a tooth of a patient.

20. The appliance of claim 19, wherein the elastic material has a plurality of holes, the holes being sized to enable the elastic material to fit around a plurality of teeth of a patient.

* * * * *